US012678035B2

(12) United States Patent
Toriihara

(10) Patent No.: US 12,678,035 B2
(45) Date of Patent: Jul. 14, 2026

(54) PHOTOGRAPHY SUPPORT DEVICE, IMAGE-CAPTURING DEVICE, AND CONTROL METHOD OF IMAGE-CAPTURING DEVICE

(71) Applicant: CANON KABUSHIKI KAISHA, Tokyo (JP)

(72) Inventor: Shigeru Toriihara, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 492 days.

(21) Appl. No.: 18/340,045

(22) Filed: Jun. 23, 2023

(65) Prior Publication Data

US 2024/0000307 A1 Jan. 4, 2024

(30) Foreign Application Priority Data

Jun. 29, 2022 (JP) ................................. 2022-104756

(51) Int. Cl.
| | |
|---|---|
| *A61B 1/24* | (2006.01) |
| *A61B 1/045* | (2006.01) |
| *A61C 9/00* | (2006.01) |

(52) U.S. Cl.
CPC ................ *A61B 1/24* (2013.01); *A61B 1/045* (2013.01); *A61C 9/0053* (2013.01)

(58) Field of Classification Search
CPC .......... A61B 1/24; A61B 1/045; A61C 9/0053
See application file for complete search history.

(56) References Cited

U.S. PATENT DOCUMENTS

| | | | |
|---|---|---|---|
| 11,723,758 B2 * | 8/2023 | Levin ................. | A61B 1/00045 348/66 |
| 11,925,320 B1 * | 3/2024 | Ahmadzadeh Saffari ................. | A61B 1/04 |
| 2015/0046184 A1 * | 2/2015 | Cocco .................... | G16H 30/20 705/3 |
| 2020/0364860 A1 * | 11/2020 | Kearney .............. | A61B 5/7267 |
| 2021/0353154 A1 * | 11/2021 | Saphier ................. | A61C 9/006 |

(Continued)

FOREIGN PATENT DOCUMENTS

| | | |
|---|---|---|
| JP | 2019-155027 A | 9/2019 |
| JP | 2020-179173 A | 11/2020 |
| JP | 2023143478 A | 10/2023 |

OTHER PUBLICATIONS

Notice of Reasons for Refusal issued by the Japanese Patent Office on Mar. 3, 2026 in corresponding JP Patent Application No. 2022-104756, with English translation.

*Primary Examiner* — Mohammed H Zuberi
(74) *Attorney, Agent, or Firm* — Carter, DeLuca & Farrell LLP

(57) ABSTRACT

A photography support device is configured to support photography of N types (where N is an integer greater than 1) of photography target parts defined in advance. The photography support device includes at least one memory and at least one processor which function as: a determining unit configured to determine, with respect to a plurality of images obtained by photography of inside of an oral cavity of a patient, which of the N types of photography target parts a photography target part in each image corresponds to; and a missing-image sensing unit configured to, based on determination results regarding each of the plurality of images, sense whether or not shooting of images of the N types of photography target parts is complete.

16 Claims, 8 Drawing Sheets

(56) References Cited

U.S. PATENT DOCUMENTS

| 2022/0369916 | A1* | 11/2022 | Carrier, Jr. | ............ | G06T 7/0012 |
| 2022/0395166 | A1* | 12/2022 | Craig | ........................ | A61B 1/07 |
| 2023/0149129 | A1* | 5/2023 | Oren-Artzi | .............. | A61B 1/24 |
| 2023/0390031 | A1* | 12/2023 | Marshall | ............... | G06T 19/006 |
| 2024/0058105 | A1* | 2/2024 | Saphier | .................. | A61C 9/004 |

* cited by examiner

Figure 2:
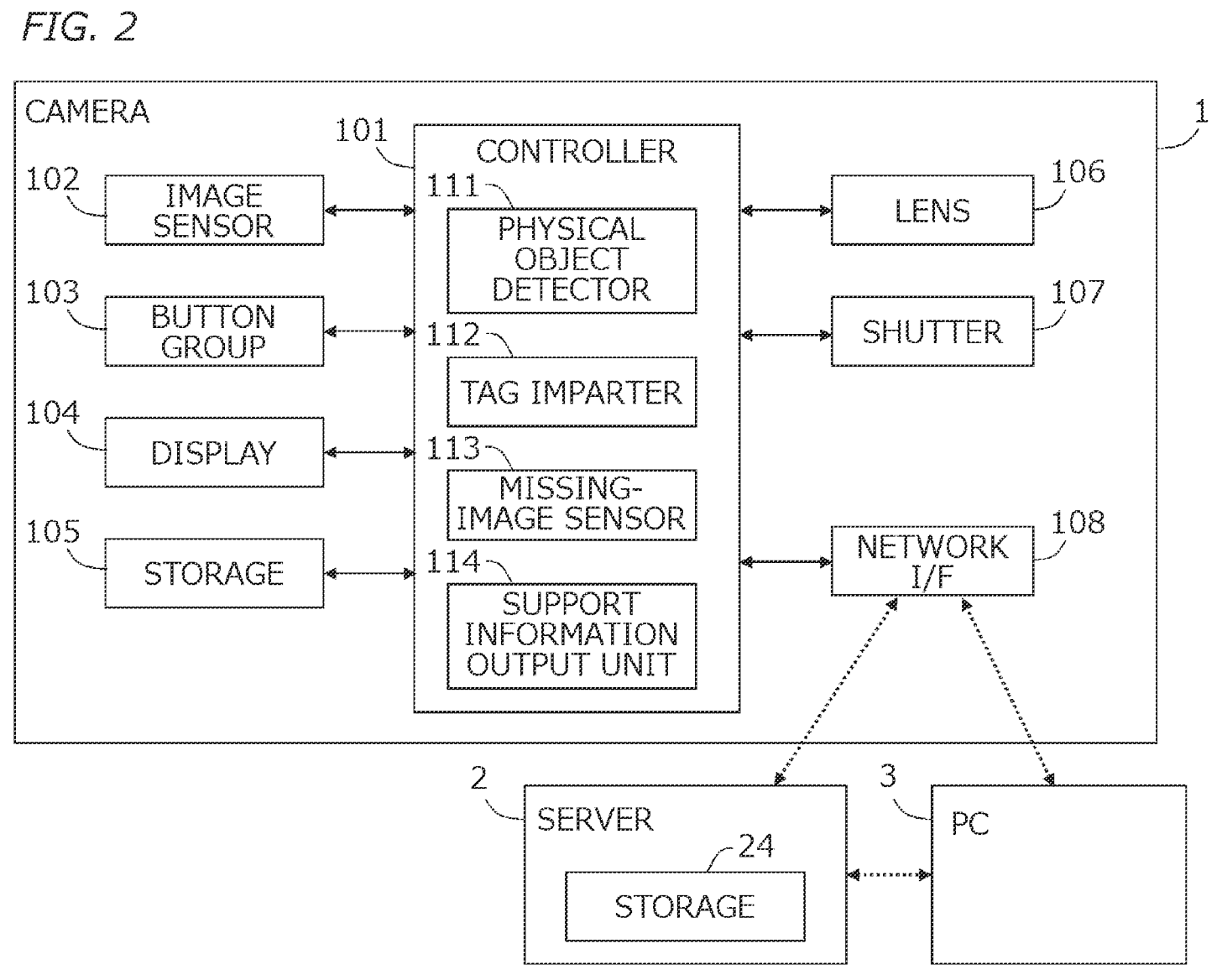

CAMERA 1

LENS 106

SHUTTER 107

NETWORK I/F 108

IMAGE SENSOR 102

BUTTON GROUP 103

DISPLAY 104

STORAGE 105

CONTROLLER 101

PHYSICAL OBJECT DETECTOR 111

TAG IMPARTER 112

MISSING-IMAGE SENSOR 113

SUPPORT INFORMATION OUTPUT UNIT 114

PC 3

SERVER 2

STORAGE 24

PHOTOGRAPHY SUPPORT DEVICE, IMAGE-CAPTURING DEVICE, AND CONTROL METHOD OF IMAGE-CAPTURING DEVICE

BACKGROUND OF THE INVENTION

Field of the Invention

The present invention relates to technology for supporting intraoral photography.

Description of the Related Art

In the practice of dentistry, a dental surgeon or a dental assistant may use a camera and take photographs of inside of the oral cavity. Intraoral images (also referred to as "intraoral photographs") are used in ascertaining the state of the teeth and gums, diagnosis, treatment, and so forth.

Japanese patent application publication No. 2020-179173 discloses a system for inputting intraoral images into a trained model, and determining the state of the oral cavity with regard to the teeth or gums. The system disclosed in Japanese patent application publication No. 2020-179173 uses a machine learning technique such as a support vector machine or the like to determine whether or not there is any camera shaking or defocus in intraoral images obtained by photography. In a case in which determination is made that there is camera shaking or defocus, processing is performed for requesting retaking of the intraoral images.

Japanese patent application publication No. 2019-155027 discloses a method for photographing the same portion of inside of the oral cavity from different directions, and generating intraoral images from which reflection portions due to saliva (hereinafter referred to as "clipped whites") have been removed, by compositing the plurality of partial images that are obtained.

In dentistry, intraoral images are one of several types of important medical information. Two points are important in order to obtain intraoral images that contribute to accurate diagnosis and treatment, one of which is to perform photography of a necessary range of the subject (rows of teeth and gums) with a correct composition (appropriate photography target part), and the other is to have no photography defects such as defocus, clipped whites, and so forth (high image quality). Accordingly, shooting intraoral images requires high-level skills and experience.

The camera shaking and defocus determination according to Japanese patent application publication No. 2020-179173 is effective in discovering photography defects, and also the removal of clipped whites according to Japanese patent application publication No. 2019-155027 enables photography defects to be corrected afterward by image processing. Accordingly, a certain degree of effects might be anticipated solving that latter problem (high image quality) by using the methods according to Japanese patent application publication No. 2020-179173 and Japanese patent application publication No. 2019-155027.

However, there conventionally has been no effective solution regarding the former problem, and whether or not photography target parts in intraoral images are appropriate has been left to the judgment and subjectivity of the photographer. Accordingly, difference (deviation) can occur with respect to range, size, orientation, position in the image, and so forth of the subject in the image, depending on the photographer. Also, in a case of a photographer with little skill, there are cases in which necessary images are not photographed (missing images), and in which photography has been performed, but the composition of photographs or the subject photographed therein is inappropriate (inappropriate images). Such flaws in images are overlooked at the time of photography, and are discovered for the first time at the stage of performing examination or tests using the images. The patient has finished the series of photography and is awaiting examination to begin, and having to perform photography of the images again at a later time in such a state not only burdens the patient timewise, but also is mentally distressing. Also, redoing the photography leads to poorer diagnosis and treatment efficiency for the clinic, which is undesirable.

SUMMARY OF THE INVENTION

The present invention provides technology for supporting shooting of appropriate intraoral images. The present invention also provides technology for supporting those without high-level skills and experience to easily shoot intraoral images.

The present disclosure includes a photography support device configured to support photography of N types (where N is an integer greater than 1) of photography target parts defined in advance, the photography support device including at least one memory and at least one processor which function as: a determining unit configured to determine, with respect to a plurality of images obtained by photography of inside of an oral cavity of a patient, which of the N types of photography target parts a photography target part in each image corresponds to; and a missing-image sensing unit configured to, based on determination results regarding each of the plurality of images, sense whether or not shooting of images of the N types of photography target parts is complete.

Further features of the present invention will become apparent from the following description of exemplary embodiments with reference to the attached drawings.

BRIEF DESCRIPTION OF THE DRAWINGS

FIG. 1 is a diagram schematically illustrating an overall configuration of an intraoral image management system;

FIG. 2 is a block diagram illustrating a configuration of a camera, a server, and a personal computer (PC);

DESCRIPTION OF THE EMBODIMENTS

Figure 3:
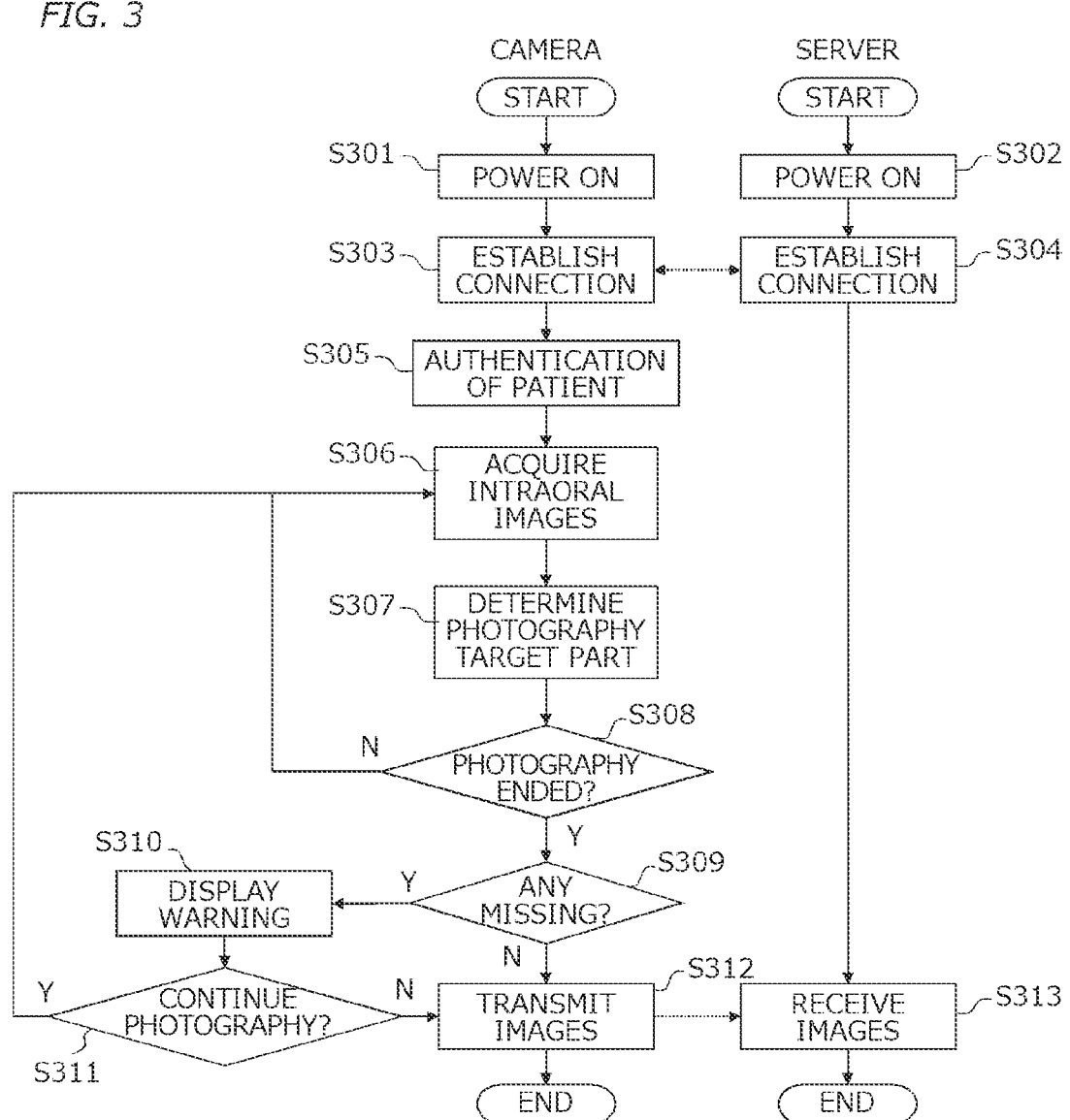
FIG. 3 is a flowchart showing processing that is executed by the camera and the server.

An embodiment of the present invention will be described with reference to the drawings. In the embodiment described below, an example will be described in which the present invention is applied to a system for shooting intraoral images used in dentistry. Note that the present invention, and the intraoral images obtained by a device according to the present invention are not limited to application to dentistry, and can be applied to various usages. For example, the intraoral images may be used for diagnosis and treatment of disorders of the mucous membrane of the oral cavity, oral care, fabrication of tools such as mouthpieces, and so forth, besides dentistry. Also, alignment of teeth and treatment marks tend to be readily preserved when the owner is met with a serious accident or disaster, and accordingly intraoral images may be used for personal authentication.

In the practice of dentistry, a dental surgeon or a dental assistant may use an image-capturing device and shoot photographs of inside of the oral cavity (In the present specification, the dental surgeon or dental assistant will be referred to as "user", and the image-capturing device as "camera". Also, the person actually operating the camera may be referred to as "photographer"). The photographer uses the camera to photograph the teeth of a patient including tooth decay and dentures, the gums including gingivitis, and so forth. At the time of photography, dental tools (assistive tools) such as cheek retractors, intraoral mirrors, and so forth are often used to eliminate blind spots and to secure field of view. Intraoral images are suitable for recording the course of the state of disorders of the teeth and of treatment. Also, intraoral images are used for ascertaining the state of the teeth and the gums, diagnosis, treatment, and so forth.

Figure 1:
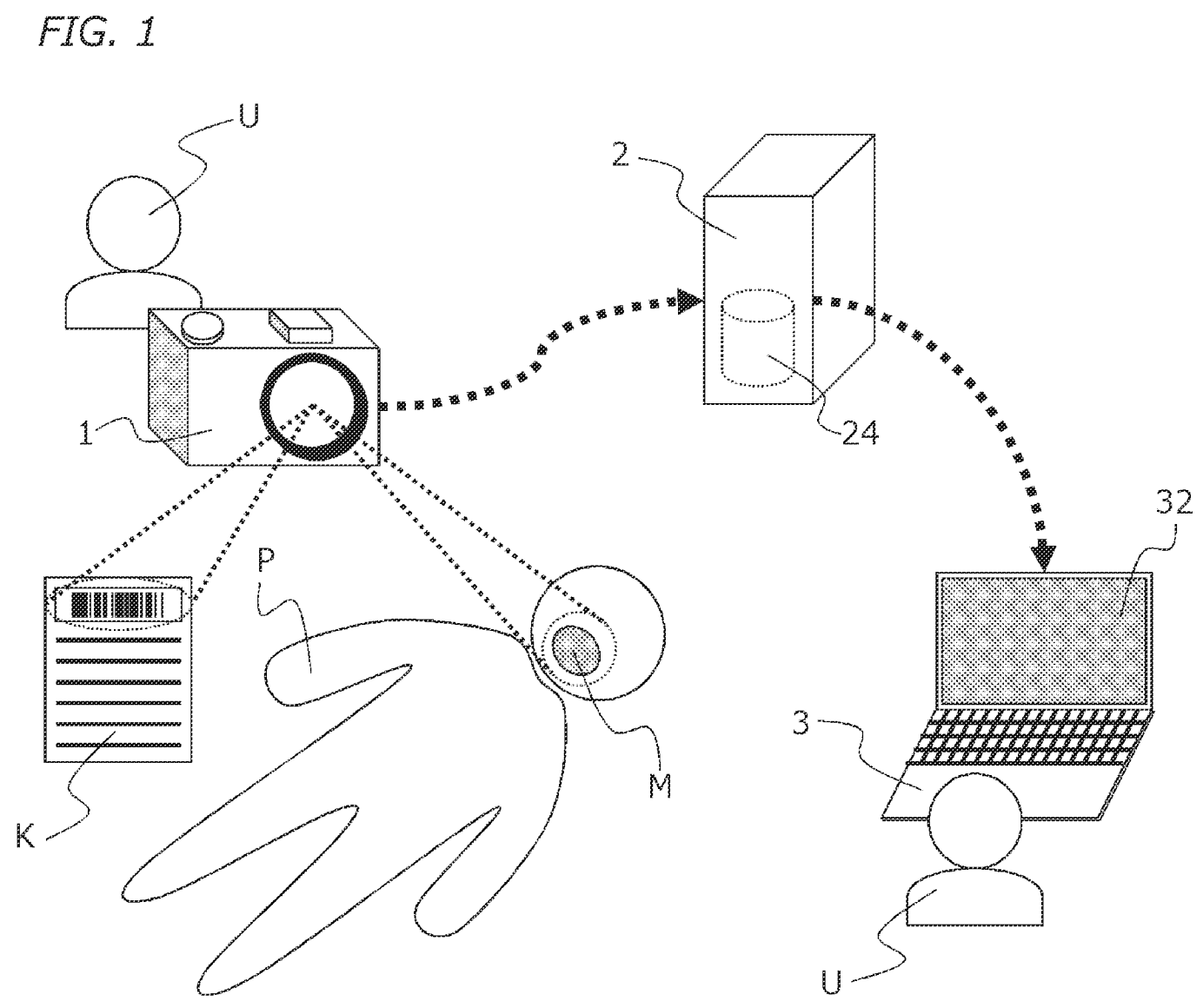

<Overall Configuration of System> FIG. 1 is a diagram schematically illustrating an overall configuration of an intraoral image management system according to the embodiment of the present invention. The intraoral image management system (hereinafter referred to simply as "system") is a system that handles photography of the oral cavity M of a patient P, and recording, managing, browsing, and so forth, of intraoral images and patient information thereof, and is used in dentistry institutions and so forth.

As a primary configuration, the intraoral image management system has a camera 1, a server 2, and a personal computer (PC) 3. The camera 1 is an image-capturing device that a user U operates and is used for photographing the oral cavity M of the patient P, photographing medical records K of the patient P, and so forth. A dental surgeon or dental assistant is assumed as the user U. The server 2 is a computer system that records and manages information relating to the patient P (patient information, medical record information, intraoral images, and so forth). The server 2 may be a physical server installed in the clinic or in a data center or the like, or may be a virtual server such as a cloud server. The PC 3 is an information processing device that the user U operates, and is used for accessing the server 2 and browsing patient information and medical record information, browsing intraoral images, entering results of examination or testing, and so forth. The camera 1, the server 2, and the PC 3 are capable of exchanging various types of information including intraoral images via a network by wireless communication or wired communication.

An overall flow of intraoral photography using the camera 1 will be described with reference to FIG. 1.

First, the patient P is made to sit or lie on an examination table, and the posture of the patient P is fixed. Dental tools such as cheek retractors, intraoral mirrors, and so forth, are inserted into the oral cavity M of the patient P as necessary, and a field of view of the rows of teeth and gums to be photographed is secured. Fixation of the posture and securing of the field of view may be performed by the patient P him/herself, of may be performed by an assistant.

The user U holds the camera 1, adjusts the composition and the focus while viewing a viewfinder or a live view image, and thereafter presses a shutter button to photograph the oral cavity M. The entirety of the inside of the oral cavity cannot be recorded in a single image, and accordingly, images of N types (where N is an integer greater than 1) of photography target parts are shot, with different ranges and compositions of the rows of teeth that are photographed. For example, in a "five-image method", five intraoral images of frontal, left side, right side, lower jaw, and upper jaw are shot. Note that the five-image method is only an example, and that the number of intraoral images to be shot and the photography target parts may be set as appropriate in accordance with the usage and object. In the present system, photography support processing by the camera 1 is performed during photography of the oral cavity M, so that users U without high-level skills and experience can appropriately and easily shoot N types of intraoral images (details to be described later).

The user U uses the camera 1 to photograph an identification mark that is applied to or printed on the medical records K (either of the photographing of the oral cavity M and the photographing of the medical records K may be performed first). Identification information for identifying the patient P is recorded in the identification mark. The camera 1 performs authentication of the patient P (confirmation of identity) on the basis of the identification information read from the identification mark, or identification information acquired from the server 2 using the information read from the identification mark as a key. Note that authentication of the patient P may be performed by a method other than the identification mark on the medical records K. For example, a method may be employed in which the camera 1 or another reader device is used to perform biometric authentication of the patient P, or a method may be employed in which the user U or the patient P enters identification information such as name and ID, or the like.

The intraoral images that shot are transmitted from the camera 1 to the server 2. The server 2 records the intraoral images that are received in storage 24, in a manner associated with information of the patient P. The user U can browse the intraoral images of the patient P stored in the server 2 using the PC 3, and make usage thereof for testing, diagnosis, studying which course of treatment to take, and so forth.

The system configuration and the flow of intraoral photography described above are only an example. For example, while the camera 1, the server 2, and the PC 3 are illustrated as separate devices in FIG. 1, the physical configuration is optional. For example, the functions of the camera 1 and the functions of the PC 3 may be implemented in a single device (As a specific configuration, a configuration can be envisioned in which a smartphone or a tablet terminal equipped with a camera is used to perform photography of the oral cavity M and the medical records K, and to browse intraoral images). Alternatively, the functions of the server 2 may be implemented in the camera 1 or the PC 3, or the functions of all of the camera 1, the server 2, and the PC 3 may be implemented in a single device. Also, while one each of the camera 1 and the PC 3 are illustrated in FIG. 1, a plurality of each of the camera 1 and the PC 3 may be employed.

<Camera> FIG. 2 is a block diagram illustrating the configuration example of the camera 1, the server 2, and the PC 3. First, the configuration of the camera 1 will be described with reference to FIG. 2.

The camera 1 is an image-capturing device used by the user U to shoot intraoral images of the patient P. Any type of camera may be used, as long as the camera is a digital camera that is capable of shooting color optical images. Single-lens reflex type cameras are suitable for high-resolution images and high-magnification images. Compact-type digital cameras are small and lightweight, and thus have an advantage in that the burden on the user U is reduced. Furthermore, cameras built into smartphones or tablet terminals may be used for shooting intraoral images.

The camera 1 includes a controller 101, an image sensor 102, a button group 103, a display 104, storage 105, a lens 106, a shutter 107, and a network interface (NI) 108. The camera 1 further includes a battery, a lighting device, and so forth (all of which are omitted from illustration).

The controller 101 is a control device that handles control of other units within the camera 1, processing of images that are shot, and other information processing. The controller 101 provides functions of a physical object detector 111, a tag imparter 112, a missing-image sensor 113, a support information output unit 114, and so forth. The physical object detector 111 has functions of extracting image features from intraoral images. The tag imparter 112 has functions of determining (estimating) photography target parts of the intraoral images based on image features, and imparting tags representing the photography target parts to the images. The missing-image sensor 113 has functions of sensing whether or not there is a photography target part that is missing. The support information output unit 114 has functions of using the results of missing-image sensing to output support information to the photographer using the camera 1.

These functions 111, 112, 113, and 114 are realized in the form of software, by the controller 101 (more specifically, a processor that the controller 101 is equipped with) executing programs stored in the storage 105. However, this configuration is not restrictive, and all or part of these functions 111, 112, 113, and 114 may be realized by a circuit such as an application-specific integrated circuit (ASIC), a field-programmable gate array (FPGA), or the like.

The image sensor 102 is a photoelectric conversion device that performs intake of photons and conversion thereof into electric signals. For example, charge-coupled devices (CCD), complementary metal-oxide-semiconductor (CMOS) sensors, and so forth, are used as the image sensor 102.

The button group 103 is a human-machine interface (HMI) for receiving operations performed by the user U. Examples of the button group 103 include physical buttons such as a shutter button, a power button, a zoom adjustment button, and so forth, and software buttons that are realized by a touch panel that the display 104 is equipped with.

The display 104 is a display device made up of a liquid crystal display, an organic electroluminescent (OEL) display, or the like. A touchscreen display is used in the present embodiment. The display 104 is used for presenting a graphical user interface (GUI) to the user U, displaying live view images (for confirmation of composition and focus), confirmation of shot images, and so forth.

The storage 105 is a non-volatile storage device capable of non-transitory storage of data, examples of which include flash memory, solid state drives, hard disk drives, and so forth. The storage 105 temporarily or permanently saves various types of information, including intraoral images.

The lens 106 is an optical system that performs image-forming of an optical image on the image sensor 102. A zoom lens is used in the present embodiment. Appropriately controlling the lens 106 enables angle of view and focus to be adjusted when photographing. The shutter 107 controls light entering the image sensor 102. Adjusting the aperture of the lens 106 and the shutter speed enables exposure to be controlled.

The Network OF (NI) 108 is a communication device for enabling exchange of data between the camera 1 and external equipment. Any standard may be used by the NI 108 for the communication format, examples of which include Wi-Fi, long-term evolution (LTE), 5G, Bluetooth (registered trademark), and so forth. Either or both of wireless communication and wired communication may be used. The camera 1 can use the NI 108 to exchange various types of information including intraoral images with the server 2, the PC 3, and other external equipment.

In the present embodiment, (the group of functions 111 to 114 of) the controller 101 realizes a photography support device that supports shooting of intraoral images by the user U, in collaboration with the display 104, the storage 105, the NI 108, and so forth. That is to say, the photography support device is implemented as a function of the camera 1. Note however that this configuration is an example, and that the camera 1 and the photography support device may be configured as separate entities.

<Server> The server 2 is a computer system that records and manages information relating to patients (patient information, medical record information, intraoral images, and so forth). The server 2 according to the present embodiment includes a central processing unit (CPU), memory, a graphics processing unit (GPU), the storage 24, an NI, and so forth. The CPU is a processor that executes programs, and governs information processing performed in the server 2. The memory is working memory that temporarily stores programs being executed by the CPU and data referenced by the programs, and so forth. The GPU is a processor specialized for graphics processing, and supports processing by the CPU. The storage 24 is a non-volatile storage device capable of non-transitory storage of data, examples of which include flash memory, solid state drives, hard disk drives, and so forth. The storage 24 temporarily or permanently saves various types of information, including intraoral images, patient information, electronic medical records, and so forth. The NI is a communication device for enabling exchange of data between the server 2 and external equipment.

<PC> The PC 3 is an information processing device that is operated by the user U. The PC 3 includes a CPU, memory, storage, a display an NI, and so forth. The CPU is a processor that executes programs, and governs information processing performed in the PC 3. The memory is working memory that temporarily stores programs being executed by the CPU and data referenced by the programs, and so forth. The storage is a non-volatile storage device capable of non-transitory storage of data, examples of which include flash memory, solid state drives, hard disk drives, and so forth. The display is a display device that presents the user U with a GUI. The NI is a communication device for enabling exchange of data between the PC 3 and external equipment. A general-use personal computer may be used as the PC 3, or a smartphone, tablet terminal, or the like, may be used.

<Shooting Intraoral Images> FIG. 3 is a flowchart showing processing executed by the camera and the server. Processing executed by the camera 1 and the server 2 will be described with reference to FIG. 3.

Step S301 is processing for turning the power of the camera 1 on. Step S302 is processing for turning the power of the server 2 on. Steps S303 and S304 are processing for the camera 1 and the server 2 to establish connection with each other. Once steps S303 and S304 have been executed, various types of information including intraoral images can be exchanged between the camera 1 and the server 2.

Step S305 is processing for the controller 101 of the camera 1 to authenticate the patient P. Once photography of the medical records K of the patient P by the user U, or input of information of the patient P, is performed, the photographed or input information is used by the controller 101 to perform authentication (confirmation of identity) of the patient P. Once the patient P is identified by the processing in step S305, the controller 101 of the camera 1 can associate the intraoral images that will be shot in step S306 with the patient P.

Step S306 is processing for the controller 101 to input an image of the oral cavity of the patient P shot by the camera 1 (intraoral image). The image that is input is stored in the storage 105. Note that the term "photography" may include both actual photographing in which the user U presses the shutter button of the camera 1 and inputs an image, and so-called "live view photography" in which the shutter button is in an unpressed state or a half-pressed state, and images are input in real time.

Step S307 is processing for the controller 101 to determine which of the N types of photography target parts, defined in advance, that the photography target part in the intraoral image shot and stored in the storage 105 in step S306 corresponds to. The determination processing in step S307 is executed by the physical object detector 111 and the tag imparter 112 of the controller 101, and will be described in detail later. A tag representing the photography target part is imparted to the intraoral image, as a result of the determination. Details of tags will be described later with reference to FIG. 4.

Step S308 is processing for the controller 101 to sense whether or not photography of the oral cavity of the patient P has ended. The method of sensing ending of photography will be described later with reference to FIGS. 5A to 5D. In a case in which the controller 101 does not sense ending of photography, the processing returns to step S306, and photography of inside of the oral cavity is continued. When the controller 101 senses ending of photography in step S308, the processing then advances to step S309.

Step S309 is processing for the controller 101 to sense whether or not there is a missing photography target part out of the N types of photography target parts that are defined, based on determination results (tags) of each of a plurality of the images stored in the storage 105. The missing-image sensing processing in step S309 is executed by the missing-image sensor 113 of the controller 101, and will be described in detail later with reference to FIG. 4. Upon the missing-image sensor 113 of the controller 101 judging that there is a photography target part that is missing, the processing advances to step S310. Upon the missing-image sensor 113 of the controller 101 judging that there are no photography target parts missing (i.e., images of all of the N types of photography target parts are present), the processing advances to step S312.

Step S310 is processing of the missing-image sensor 113 of the controller 101 displaying a warning on the display 104. This warning is to notify the user U to the effect that there is a missing photography target part remaining. Step S311 is processing for the controller 101 to confirm intent of the user U with respect to the warning displayed in step S310. The controller 101 displays a UI on the display 104 querying whether or not to continue photography, and prompts the user U for input, for example. An example of the warning display and an example of confirmation of intent of the user U will be described later with reference to FIGS. 6A and 6B. In a case in which the user U specifies continuing photography, the controller 101 returns the processing to step S306. Conversely, in a case in which the user U does not select continuation of photography, the controller 101 advances the processing to step S312.

Step S312 is processing for the controller 101 to transmit various types of information, including the intraoral images, to the server 2. Step S313 is processing for the server 2 to receive various types of information, including the intraoral images, from the camera 1.

Note that the executing entities of steps S301 to S313 is not limited to the configuration in the embodiment described above. For example, all or part of the functions of determination processing in step S307, in which the processing load is great, may be executed at the server 2. The server 2 normally has higher processing capabilities as compared to the controller 101 of the camera 1, and accordingly executing processing with a great load at the server 2 realizes processing with good efficiency.

Figure 4:
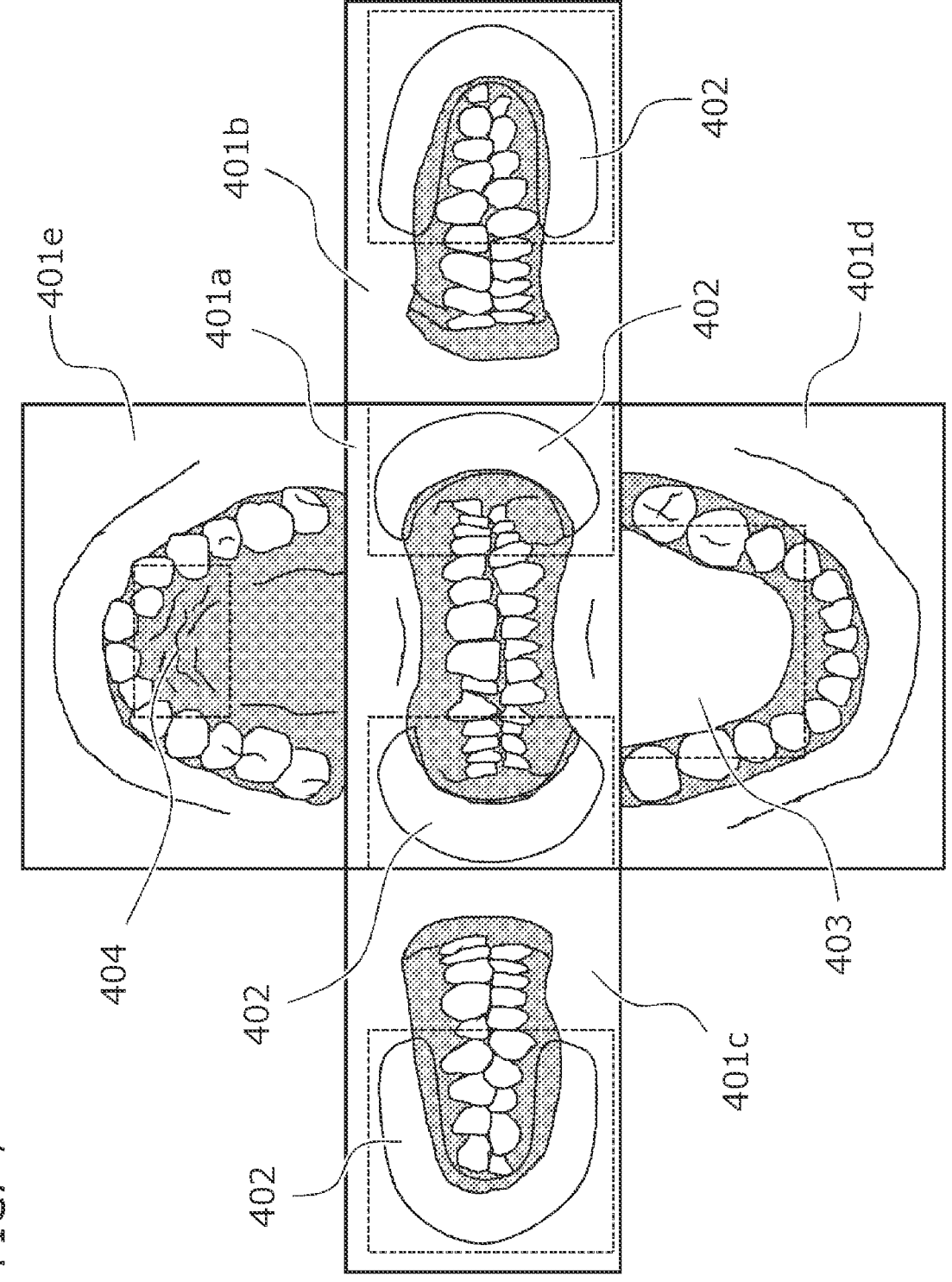
FIG. 4 is a diagram illustrating intraoral images (five-image method) shot by the camera, and feature objects.

<Example of Intraoral Images> FIG. 4 is a diagram illustrating examples of intraoral images (five-image method) shot by the camera, and feature objects included in the intraoral images.

The feature objects in the intraoral images detected by the physical object detector 111, and tags imparted to the intraoral images, will be described with reference to FIG. 4.

The five images illustrated in FIG. 4 are an image group obtained by the user U performing photography of different photography target parts inside of the oral cavity of the patient P. Each of five images 401a to 401e corresponds to a respective one of the five types of photography target parts. (In the following description, the term "image" basically refers to a single image corresponding to one photography target part, but may refer to a plurality of images corresponding to a plurality of photography target parts, depending on the context. Terms such as "image group" or "image set" may be used to explicitly indicate a plurality of images.)

The intraoral image group illustrated in FIG. 4 is made up of the five images of a frontal image 401a, a left-side image 401b, a right-side image 401c, a lower-jaw image 401d, and an upper-jaw image 401e. The frontal image 401a is an image shot of a frontal view of the patient P. The left-side image 401b is an image shot of a left-side view of the patient P, and the right-side image 401c is an image shot of a right-side view of the patient P. The lower-jaw image 401d is an image shot of a lower-jaw occlusion face view of the patient P, and the upper-jaw image 401e is an image shot of an upper-jaw occlusion face view of the patient P. The method of photographing the five types of photography target parts of the frontal view, the left-side view, the right-side view, the lower-jaw occlusion face view, and the upper-jaw occlusion face view, described above, is called the "five-image method". The five-image method is in widespread use, due to being able to record generally the entirety of the rows of teeth of the patient P. Note that besides the five-image method, known methods of shooting intraoral images also include a three-image method, a nine-image method, a twelve-image method, and so forth, and any of the shooting methods may be used in accordance with usage and object. Also, photography is not limited to these existing photography methods, and photography of unique photography target parts may be performed.

When shooting intraoral images, it is common to use a dental tool called a cheek retractor 402, in order to eliminate blind spots dur to being covered by the corners of the mouth. It can be seen in FIG. 4 that in the intraoral images according to the five-image method, the cheek retractors 402 are in the frontal image 401*a*, the left-side image 401*b*, and the right-side image 401*c*.

The physical object detector 111 is configured to detect the cheek retractors 402 in the intraoral images.

In the frontal image 401*a*, the cheek retractors 402 are detected to the left side and the right side of the rows of teeth. Accordingly, when the cheek retractors 402 are detected by the physical object detector 111 in both of a left-side region and a right-side region in an intraoral image, the tag imparter 112 determines that the photography target part of this intraoral image is the frontal view, and imparts a tag named "Frontal" to this intraoral image.

In the left-side image 401*b*, the cheek retractor 402 is detected to the right side of the rows of teeth. Accordingly, when the cheek retractor 402 is detected by the physical object detector 111 in only the right-side region in the intraoral image, the tag imparter 112 determines that the photography target part of this intraoral image is the left-side view, and imparts a tag named "Left Side" to this intraoral image.

In the right-side image 401*c*, the cheek retractor 402 is detected to the left side of the rows of teeth. Accordingly, when the cheek retractor 402 is detected by the physical object detector 111 in only the left-side region in the intraoral image, the tag imparter 112 determines that the photography target part of this intraoral image is the right-side view, and imparts a tag named "Right Side" to this intraoral image.

In photography of the left-side view and the right-side view, there are cases in which an intraoral mirror is used in addition to the cheek retractors 402, in order to fully photograph as far back as the molars. Using the intraoral mirror causes the right and left in the image to be inverted, and accordingly, the position of the cheek retractor 402 in the intraoral image differs depending on whether a case in which the intraoral mirror is used and a case in which the intraoral mirror is not used. Accordingly, determination logic for the photography target part by the tag imparter 112 may be switched to an intraoral mirror mode, either by the user U instructing the camera 1 regarding the presence of the intraoral mirror by the button group 103, or the controller 101 automatically sensing the present of the intraoral mirror from the image.

Also, the physical object detector 111 is configured to detect the tongue 403 in the intraoral image. For example, in the lower-jaw image 401*d*, the tongue 403 is in the image, occupying the middle portion of the upper half thereof. Conversely, the tongue 403 is not in the other images 401*a* to 401*c* and 401*e*. Accordingly, when the physical object detector 111 detects the tongue 403 at the middle region of an intraoral image, the tag imparter 112 determines that the photography target part of this intraoral image is the lower-jaw occlusion face view, and imparts a tag named "Lower Jaw" to this intraoral image.

Also, the physical object detector 111 is configured to detect palate ridges 404 in the intraoral image. For example, in the upper-jaw image 401*e*, the palate ridges 404 are detected at an approximately middle portion (in a region on an inner side of a parabolic array of the row of teeth) in the image. Conversely, the palate ridges 404 are not in the other images 401*a* to 401*d*. Accordingly, when the physical object detector 111 detects the palate ridges 404 at the middle region of an intraoral image, the tag imparter 112 determines that the photography target part of this intraoral image is the upper-jaw occlusion face view, and imparts a tag named "Upper Jaw" to this intraoral image.

In the determination processing in step S307 in FIG. 3, preferably, the physical object detector 111 detects the feature object (cheek retractor, tongue, or palate ridges) in the intraoral image, and the tag imparter 112 determines the photography target part in the intraoral image based on image features, such as the presence or absence of feature objects, the positions of feature objects, and so forth, in the image. The tag imparter 112 then imparts the tags representing the photography target parts to the intraoral images. In a case of photographing using the five-image method, one of the five types of tags that are "Frontal", "Left Side", "Right Side", "Lower Jaw", and "Upper Jaw" is imparted to each respective intraoral image.

In the missing-image sensing processing in step S309 in FIG. 3, the missing-image sensor 113 checks the tags of each of the plurality of intraoral images of the patient P stored in the storage 105, and judges whether the five types of tags are all present, i.e., whether there is no missing tag (photography target part). When the five types of tags are all present, this means that photography according to the five-image method has been completed (correctly performed).

The cheek retractor 402 that has been noted in the present embodiment has a known color and shape, and the position and size in the image is also generally determinate. In the same way, the positions, shapes, and so forth of the tongue 403 and the palate ridges 404 in the image are also generally determinate. Accordingly, detecting these feature objects by image recognition is not difficult. The physical object detector 111 may use classical machine learning, of which support vector machines are representative, as an algorithm for detecting feature objects, or may use algorithms based on deep learning, such as Region-based Convolutional Neural Networks (R-CNN), You Only Look Once (YOLO), Single Shot MultiBox Detector (SSD), Deep Contextual Network (DCN), and so forth. For example, in a case of a machine learning algorithm such as a support vector machine or the like, the physical object detector 111 detects feature objects from an input image (image of which the photography target part is unknown), using a trained model that has performed machine learning regarding the correlation between image features extracted from the image and the feature objects. In a case of a deep learning algorithm, the physical object detector 111 detects feature objects from an input image (image of which the photography target part is unknown), using a trained model acquired by deep learning using training data made up of a great number of images labeled with correct answer labels (supervised information) of feature objects. Note that the trained model may output, in addition to information of the name of the feature object and the position in the image as detection results, information of probability (also referred to as certainty, likelihood, or reliability) of the detection results. The higher the probability of the detection results is, the higher the probability of the determination results regarding the photography target part is. Accordingly, the probability of the detection results can be rephrased as being the probability of the determination results.

Note that the physical object detector 111 according to the present embodiment is configured to detect the three feature objects of the cheek retractor 402, the tongue 403, and the palate ridges 404, but the objects of detection by the physical object detector 111 are not limited to these. For example, teeth, rows of teeth, gums, lips, and so forth, may be detected as feature objects, and other structures or tissues inside of the oral cavity (including those for which there are no general names), or features in the intraoral images that are not recognizable by humans, may be selected as the objects of detection.

Also, the photography target part is determined in the above embodiment by the two steps of a step of detecting a feature object from the image by the physical object detector 111 and a step of determining the photography target part on the basis of the presence or absence and of the feature objects and the position thereof, but the photography target part may be determined directly from the image. For example, in a case of a machine learning algorithm such as a support vector machine or the like, the controller 101 determines a photography target part from an input image (image of which the photography target part is unknown), using a trained model that has performed machine learning regarding correlation between the image features extracted from the image and the photography target parts. Examples of image features that can be extracted from images include color, luminance, shape, placement, edge, count, spatial frequency, and so forth. In a case of a deep learning algorithm, the controller 101 determines a photography target part from an input image (image of which the photography target part is unknown), using a trained model acquired by deep learning using training data made up of a great number of intraoral images labeled with correct answer labels (supervised information) of photography target parts. Note that the trained model may output, in addition to information of the photography target part as determination results, information of probability (also referred to as certainty, likelihood, or reliability) of the determination results.

Note that the tags to be imparted to the intraoral images are "Frontal", "Left Side", "Right Side", "Lower Jaw", and "Upper Jaw" in the present embodiment, but this is not necessarily restrictive. The tags do not need to be names that are recognizable to humans.

<Sensing Ending of Photography> FIGS. 5A to 5D are diagrams illustrating example of a UI for ending photography of inside of the oral cavity. An example of a method for sensing ending of photography in step S308 will be described with reference to FIGS. 5A to 5D.

Figures 5A, 5B, 5C, 5D:
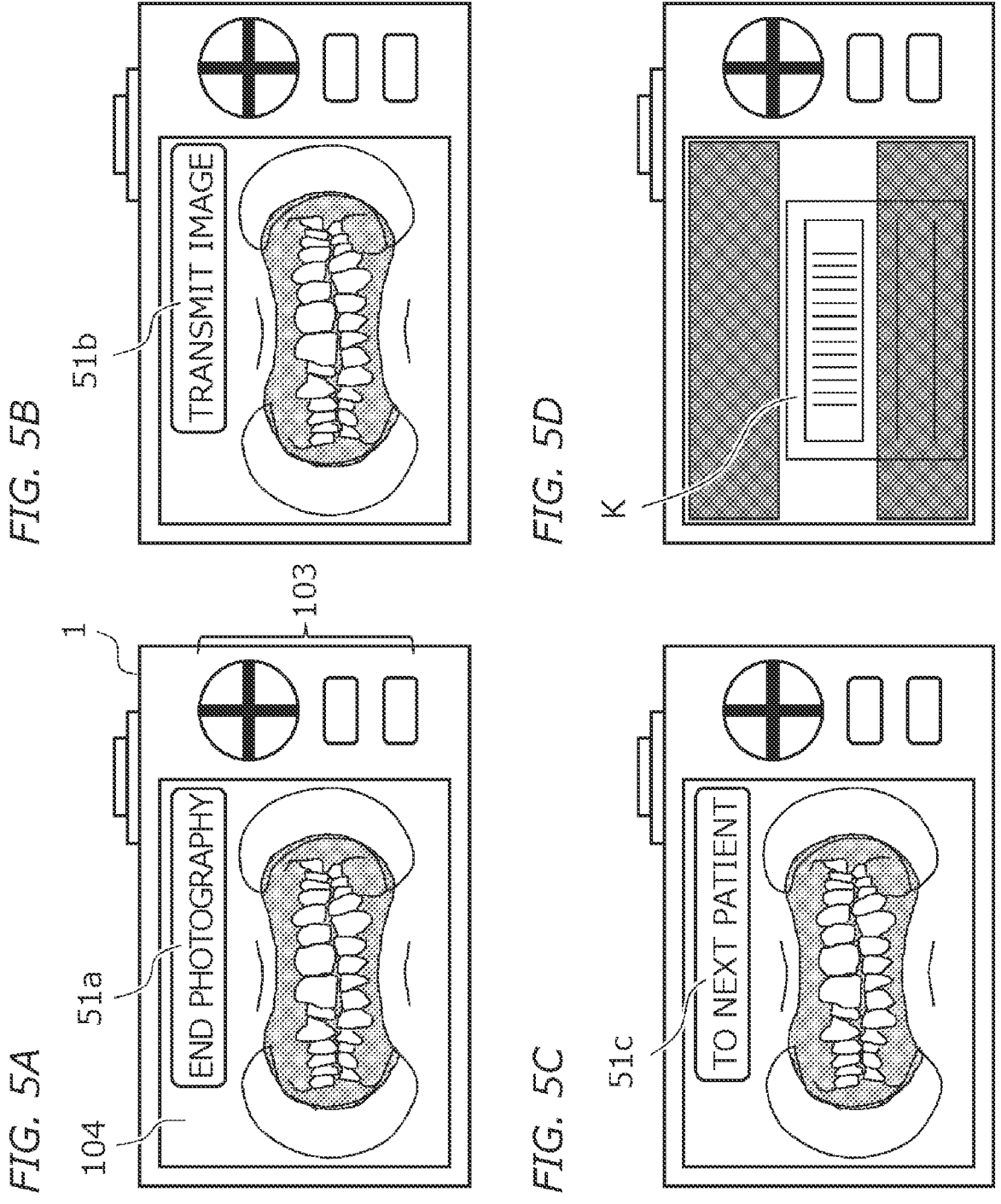
FIGS. 5A to 5D are diagrams illustrating user interfaces (UI) for ending intraoral photography.

An "End Photography" button 51a is displayed on the display 104 of the camera 1 illustrated in FIG. 5A. When the user U wants to end photography of inside of the oral cavity of the patient P, the user U operates the button group 103 (including the touch panel that the display 104 is equipped with) and presses the "End Photography" button 51a. Upon sensing that the "End Photography" button 51a has been pressed, in step S308 the controller 101 judges that ending of photography has been reached.

A "Transmit Image" button 51b is displayed on the display 104 of the camera 1 illustrated in FIG. 5B. When the user U wants to transmit the intraoral image of the patient P that has been shot to the server 2, the user U operates the button group 103 (including the touch panel that the display 104 is equipped with) and presses the "Transmit Image" button 51b. Upon sensing that the "Transmit Image" button 51b has been pressed, in step S308 the controller 101 judges that ending of photography has been reached.

A "To Next Patient" button 51c is displayed on the display 104 of the camera 1 illustrated in FIG. 5C. When the user U wants to switch the patient of which the inside of the oral cavity is being photographed, the user U operates the button group 103 (including the touch panel that the display 104 is equipped with) and presses the "To Next Patient" button 51c. Upon sensing that the "To Next Patient" button 51c has been pressed, in step S308 the controller 101 judges that ending of photography has been reached.

The identification mark of the medical records K of the patient P that the user U has photographed is displayed on the display 104 of the camera 1 illustrated in FIG. Upon sensing that an identification mark of a patient X that is different from the patient P authenticated in step S305 has been photographed, the controller 101 judges that the patient to be photographed has switched from P to X, i.e., that the photography of the patient P has ended.

Figure 6A:
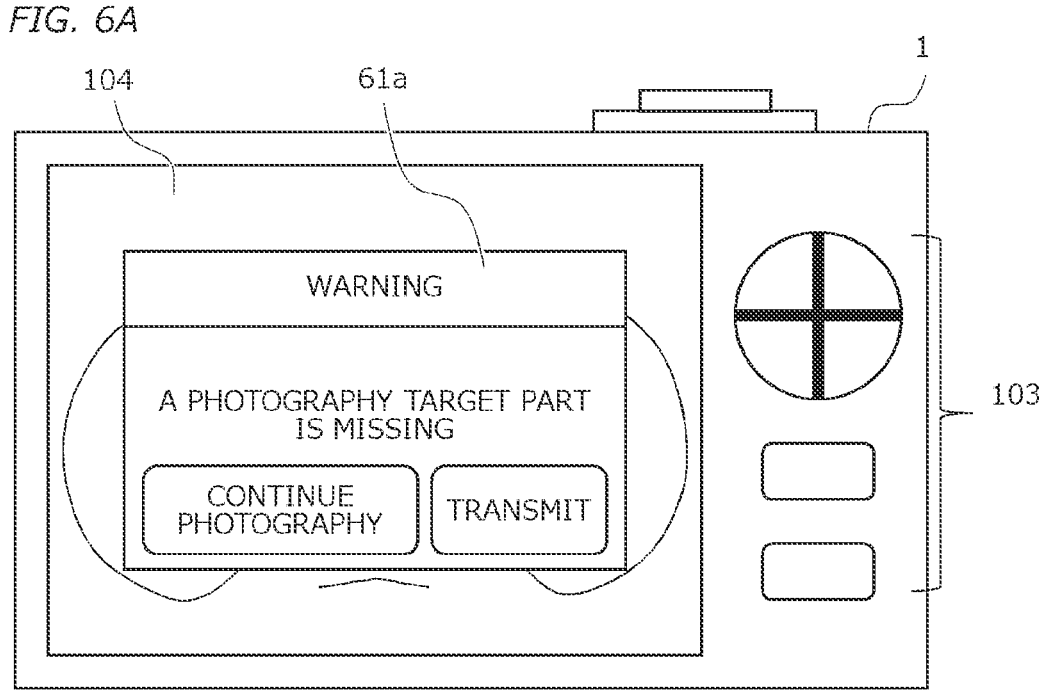
FIGS. 6A and 6B are diagrams illustrating warning dialogues that are brought up upon sensing missing photography target parts.
Figure 6B:
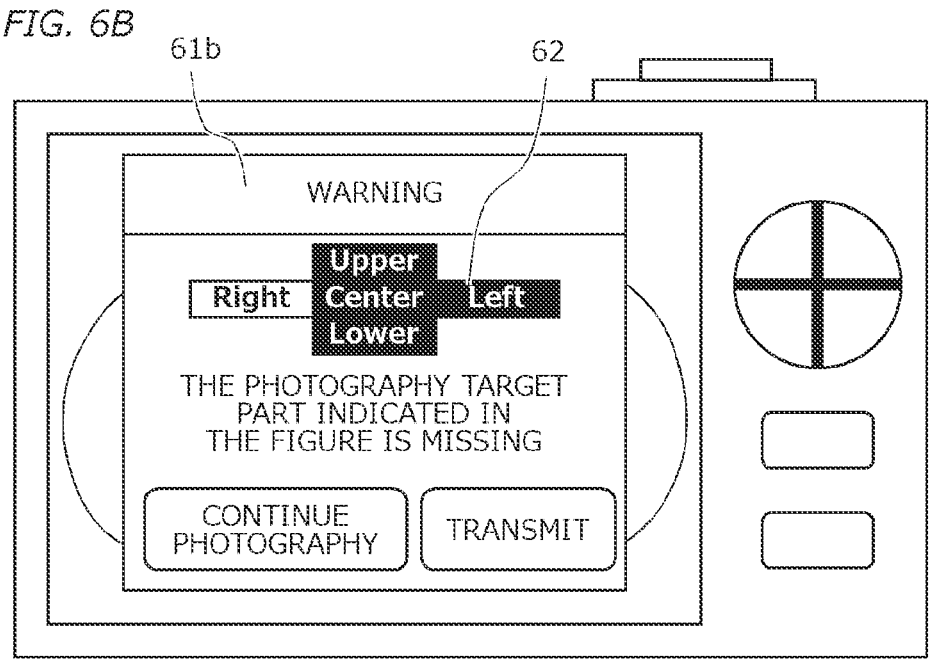

<Examples of Warnings> FIGS. 6A and 6B are diagrams illustrating warning dialogues that are displayed upon sensing missing intraoral images. The GUI and dialogues that notify the user U of missing intraoral images of the patient P will be described with reference to FIGS. 6A and 6B.

Upon the controller 101 sensing ending of photography in step S308, in step S309 the missing-image sensor 113 references the tags of the intraoral images of the patient P stored in the storage 105, and confirms whether or not there are missing photography target parts. In the case of photography according to the five-image method, the missing-image sensor 113 confirms whether images of all five types of photography target parts, which are "frontal", "left side", "right side", "lower jaw", and "upper jaw", are present. If even one is missing, the support information output unit 114 displays a warning dialog 61a, illustrated in FIG. 6A, on the display 104 of the camera 1. The warning dialog 61a notifies the user U (photographer) to the effect that there is a missing photography target part, and queries the user U (photographer) whether to continue photography or to transmit the intraoral images to the server 2. In a case in which "Continue Photography" is selected by the user U, the processing returns to step S306, and the next intraoral image is input. Conversely, in a case in which "Transmit" is selected by the user U, the processing advances to step S312. In step S312, the controller 101 transmits the photography-completed intraoral image group of the patient P stored in the storage 105 to the server 2, regardless of the missing images.

FIG. 6B is another example of a warning screen. A warning dialog 61b, illustrated in FIG. 6B, is displayed on the display 104 of the camera 1. In the warning dialog 61b, the missing photography target parts out of the photography target parts for the five-image method are explicitly indicated, in addition to the display content of the warning dialog 61a. In the display example in FIG. 6B, the support information output unit 114 displays an indicator 62 (hereinafter referred to as "photography-completed indicator") made up of five icons (shapes) indicating the photography status of the respective five photography target parts, on the display 104. Icons of the missing photography target parts are displayed in a different form from the icons of the photography-completed photography target parts. This photography-completed indicator 62 is an example of support information indicating that there is a missing photography target part. The user U can easily see that there is a photography target part that has not been photographed yet, or of which photography has been overlooked, by viewing the warning dialog 61b.

<Real-Time Notification of Status of Photography> The photography-completed indicator 62 in FIG. 6B may be displayed only in a case in which a missing photography target part remains after ending photography, but similar support information may be used for real-time notification of the status of photography.

Figure 7:
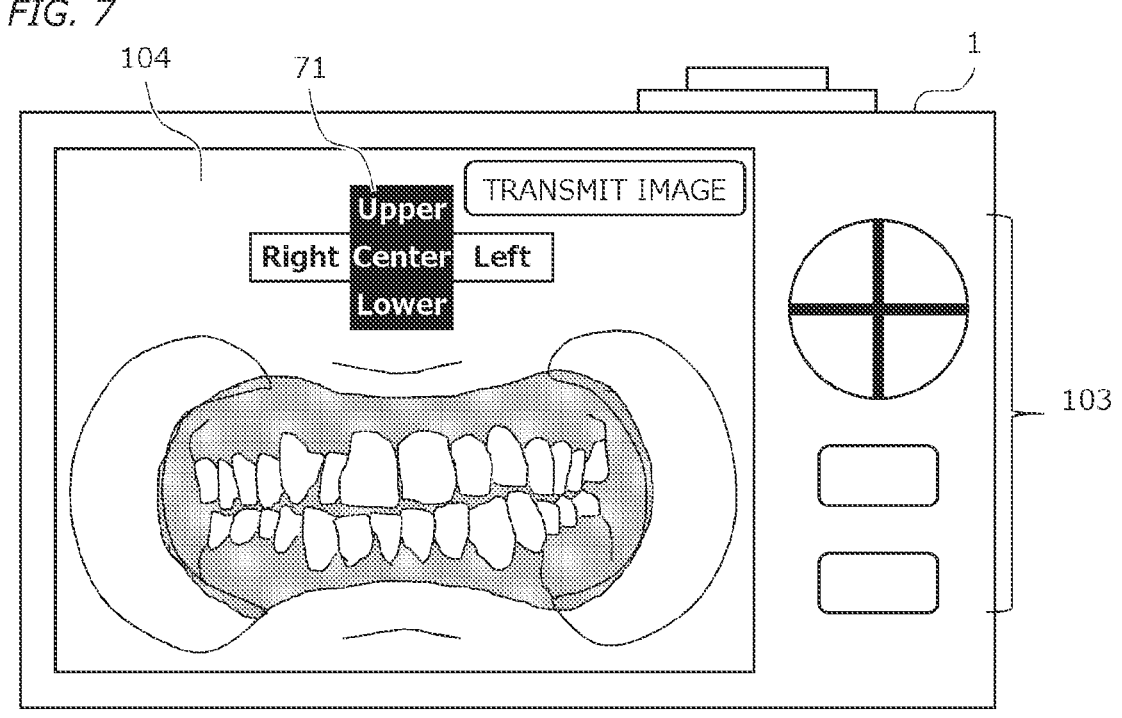
FIG. 7 is a diagram illustrating a UI of a real-time notification of a photography status.

FIG. 7 is a diagram illustrating a UI for real-time notification of the status of photography. The support functions for causing the user U who is photographing the oral cavity of the patient P to ascertain already-photographed photography target parts and missing photography target parts in real time will be described with reference to FIG. 7.

Upon the patient P being authenticated in step S305 in FIG. 3, and photography being started in step S306, the support information output unit 114 performs on-screen display (OSD) of a photography-completed indicator 71 illustrated in FIG. 7 upon a live view image on the display 104. This photography-completed indicator 71 is preferably displayed on the display 104, either constantly or at necessary timings, while photography of the patient P is being performed (i.e., while the loop of steps S306 to S308 in FIG. 3 is being executed).

FIG. 7 illustrates the photography-completed indicator 71 for the five-image method. The photography-completed indicator 71 is made up of five icons, indicating the status of photography of the five photography target parts. In an initial state, the five icons are all displayed filled in with white (representing unphotographed).

Upon inside of the oral cavity of the patient P being photographed by the user U, the controller 101 inputs the image thereof (step S306 in FIG. 3), and determines the photography target part of the intraoral image based on image features, and imparts a tag (step S307). At this time, the support information output unit 114 updates the display of the photography-completed indicator 71 so that the icon corresponding to the photography target part photographed this time is filled in with black (representing photography-completed).

For example, when an intraoral image to which the "Frontal" tag is imparted is saved in the storage 105 of the camera 1, the support information output unit 114 fills in the "Center" icon of the photography-completed indicator 71 with black. In the same way, when the "Left Side" tag, a "Left" icon is filled in with black, when the "Right Side" tag, a "Right" icon is, when the "Lower Jaw" tag, a "Lower" icon is, and when the "Upper Jaw" tag, an "Upper" icon is. The display example in FIG. 7 illustrates a state in which the "upper jaw", "frontal" and "lower jaw" images are photography-completed, and the "left side" and "right side" images are unphotographed.

Upon the intraoral images being transmitted in step S312, the photography-completed indicator 71 is initialized, and the icons of all photography target parts return to being filled in with white.

While photography of inside of the oral cavity of the patient P is being performed, the user U can ascertain photography-completed photography target parts and unphotographed photography target parts in real time, due to the photography-completed indicator 71 being displayed. This has the effects of photography work proceeding smoothly, as well as preventing photography target parts from being overlooked.

<Selection of Transmission Images> Next, image-selection support functions that the support information output unit 114 provides will be described.

There may be cases in which photography fails, or images of determined composition or images of the quality that the user U desires not being able to be successfully shot, due to camera shake occurring or the patient P moving during photography. Accordingly, in actual practice of dentistry, there is demand for operation in which the same photography target part is photographed a plurality of times, and the best image is selected out of the obtained image group (referred to as "candidate image group") and transmitted to the server 2. Be that as it may, the work for selecting the image to transmit from the plurality of candidate images is troublesome and time-consuming. Also, this depends on the subjectivity and the judgment of the user U, and accordingly there is a possibility that an appropriate image may not be selected. There also is a problem in that confirming the composition and quality of images on the display 104 of the camera 1, which is small, is difficult in the first place.

Figure 8:
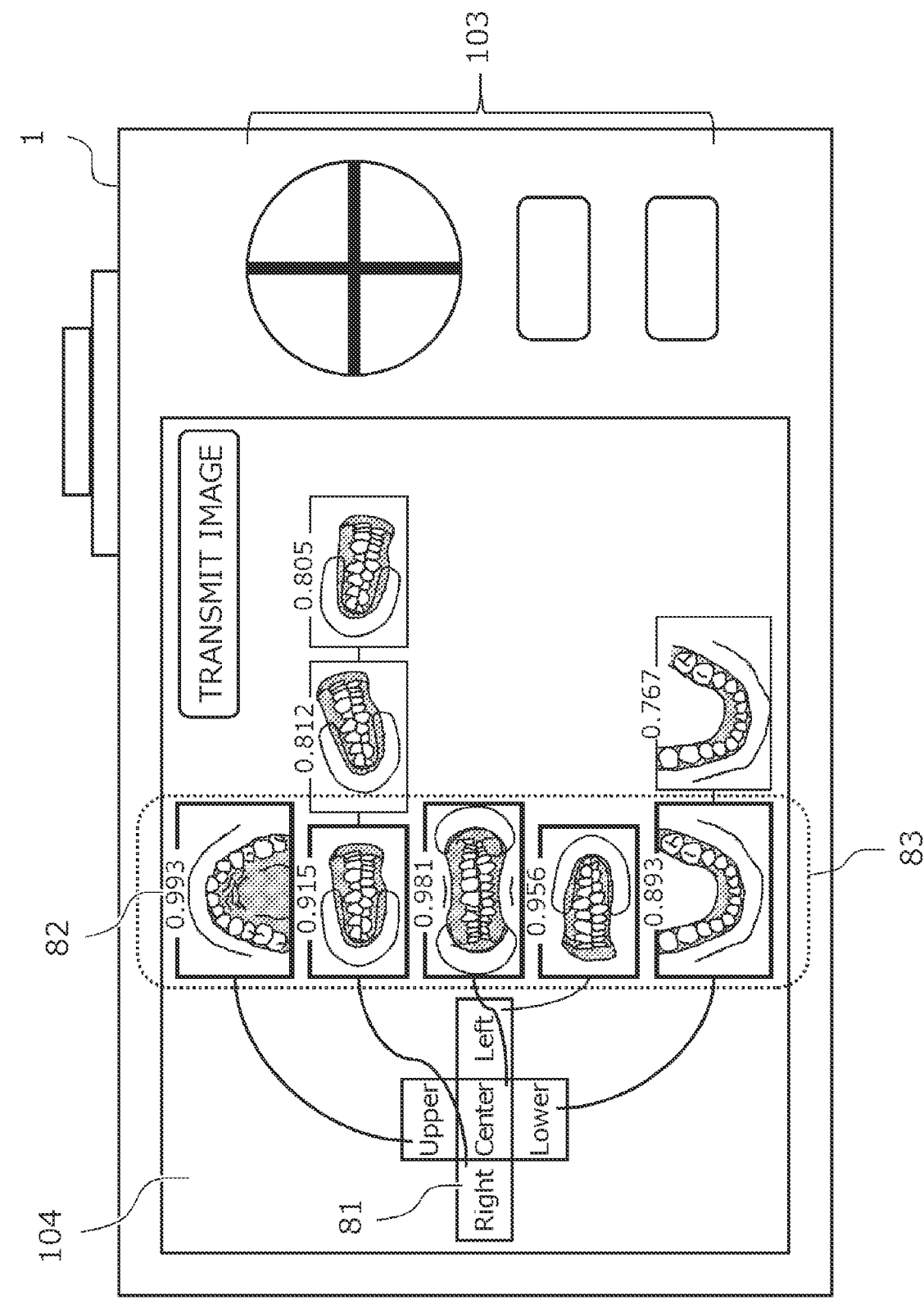
FIG. 8 is a diagram illustrating an image-selection graphical user interface (GUI) that mage-selection support functions provide.

Accordingly, the support information output unit 114 of the controller 101 assists in selection of transmission images by the user U, through the image-selection support functions illustrated in FIG. 8. FIG. 8 is a diagram illustrating an image-selection GUI that the image-selection support functions provide.

Upon the processing in step S312 in FIG. 3 being started, the support information output unit 114 references the image group of the patient P that is stored in the storage 105, and confirms whether there are duplicate images of the same photography target part. In a case in which duplicate candidate images are present for the same photography target part (i.e., in a case in which the same tag is imparted to a plurality of images), the support information output unit 114 displays the image-selection GUI illustrated in FIG. 8 on the display 104 before executing image transmission to the server 2.

A photography-completed indicator 81 is displayed to the left side of the screen in the image-selection GUI. The user U can confirm the specifications (five-image method in the example in FIG. 8) for the image set to be transmitted to the server 2 using this photography-completed indicator 81.

The intraoral images to which tags representing the photography target part have been imparted are displayed to the right side of the screen in the image-selection GUI, grouped by the photography target part. In the example in FIG. 8, the upper jaw image is displayed in the first row, the right-side images are displayed in the second row, the frontal image is displayed in the third row, the left-side image is displayed in the fourth row, and the lower-jaw images are displayed in the fifth row. In a case in which a plurality of candidate images exist for the same photography target part (the right-side images and the lower-jaw images in the example in FIG. 8), the plurality of candidate images are displayed arrayed in the lateral direction. Note that in a case in which the number of candidate images is great and not all can be displayed on the screen, arrangements may be made such as enabling images displayed on the screen to be switched by a scroll display, displaying images overlapped, or the like.

A label 82 indicating certainty is attached to each intraoral image. The certainty is information obtained in the determination processing of the photography target parts of the intraoral images, and is an index indicating the probability of the determination results with respect to that intraoral image. The highest value for certainty is 1.0, and the smaller the value is, this indicates that the chances of erroneous determination are that much higher. In a case in which a plurality of candidate images exist for the same photography target part, the support information output unit 114 places the candidate image with the highest certainty to the far left, and decides the positions for the remaining candidate images so as to be arrayed in descending order of certainty from the left to the right.

In the initial state of the image-selection GUI, the candidate images with the highest certainty for each of the photography target parts are displayed arrayed vertically in a column to the far left, as illustrated in FIG. 8. Five images 83 in the column to the far left that is surrounded by a dashed line are the image set selected as the objects of transmission to the server 2. The images selected as being the object of transmission preferably are displayed in a form so as to be distinguishable from the remaining images. Although the images that are the object of transmission are surrounded by heavy line frames in the example in FIG. 8, other methods (e.g., attaching an icon (badge) indicating selection, changing the size of the image, etc.) may be used. The user U can rearrange the array of images by operating the button group 103 (including dragging operations of the images on the display 104), thereby optionally changing the image set that is the object of transmission. That is to say, when the user U recognizes there is an image with better composition or image quality than the candidate image selected (recommended) by the support information output unit 114, the image that is the object of transmission may be changed. Thereafter, upon the user U pressing the "Transmit Image" button, the image group that the controller 101 has selected as the object of transmission is transmitted to the server 2.

The user U can easily select images with appropriate composition and image quality from a plurality of candidate images by using the image-selection support functions described above. Particularly, the image-selection GUI according to the present embodiment enables the user U to perform image selection operations while confirming and understanding the specifications (number, photography target parts, etc.) of images to be transmitted to the server 2, through display of the indicator 81. Also, the candidate images are grouped and displayed by photography target part, which facilitates visual comparison among images of the same photography target part for the user U. Moreover, information of certainty is displayed along with the image, and accordingly the user U can select the images to be transmitted while referencing the objective index of certainty, in addition to the appearance (subjective evaluation) of the image. Thus, selection of appropriate images is facilitated, and also an advantage is manifested in that variance due to individual subjectivity can be reduced. Further, while the image-selection GUI automatically recommends images with the highest certainty as the objects of transmission, the user U can easily change the objects of transmission, and accordingly the labor and time expended for image selection can be minimized.

Note that the configuration of the image-selection GUI is not limited to that illustrated in FIG. 8. The image-selection GUI may display all photography-completed images of the patient P as candidate images, or may display just part of the images selected from the photography-completed images as candidate images. For example, just images of which the certainty is no less than a predetermined threshold value may be taken as candidate images, or a certain number of images in order from the greatest certainty may be taken as candidate images. Further, all N types of photography target parts may be displayed, or a method may be used in which just photography target parts regarding which there are a plurality of images (the right-side images and the lower-jaw images in the example in FIG. 8) are displayed in the image-selection GUI. In a case in which the number of photography-completed images is great, such refinement of candidate images enables the viewability and usability of the image-selection GUI to be improved.

According to the camera 1 that is equipped with the photography support device according to the present embodiment described above, those without high-level skills and experience can easily shoot intraoral images that satisfy required specifications (number, composition, quality).

According to the present disclosure, shooting of appropriate intraoral images can be supported. Also, those without high-level skills and experience can easily shoot necessary intraoral images.

<Other Embodiments> Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-104756, filed on Jun. 29, 2022, which is hereby incorporated by reference herein in its entirety.

What is claimed is:

1. A photography support device configured to support photography of N types (where N is an integer greater than 1) of photography target parts defined in advance, the photography support device comprising at least one memory and at least one processor which function as:

a determining unit configured to determine, with respect to a plurality of images obtained by photography of inside of an oral cavity of a patient, which of the N types of photography target parts a photography target part in each image corresponds to, and to output a certainty that indicates a probability of determination results, along with the determination results of the photography target part in each image;

a missing-image sensing unit configured to, based on the determination results regarding each of the plurality of images, sense whether or not shooting of images of the N types of photography target parts is complete; and a support information output unit configured to output information for supporting photography of the N types of photography target parts by a photographer, using at least one of the determination results by the determining unit, and sensing results by the missing-image sensing unit, wherein the support information output unit displays all or part of the plurality of images as a plurality of candidate images, and outputs an image-selection graphical user interface (GUI) by which the photographer is caused to select an image from the plurality of candidate images, and wherein the support information output unit displays, in the image-selection GUI, the plurality of candidate images in a manner of being grouped by the photography target part, and displays, in the image-selection GUI, certainty information of each candidate image along with the plurality of candidate images.

2. The photography support device according to claim 1, wherein in a case in which a photography target part that is missing is sensed by the missing-image sensing unit, the support information output unit performs notification to the photographer.

3. The photography support device according to claim 2, wherein the support information output unit performs the notification at a timing of ending of photography of the patient.

4. The photography support device according to claim 3, wherein the timing of ending of photography of the patient is one timing of a timing of sensing an instruction for ending of photography, a timing of sensing an instruction for externally transmitting the images, and a timing of sensing switching of the patient to be photographed.

5. The photography support device according to claim 1, wherein the support information output unit outputs a status of photography indicating whether photography-completed or unphotographed, while photography of the patient is being performed, for each of the N types of photography target parts.

6. The photography support device according to claim 5, wherein the support information output unit displays N shapes indicating the status of photography for each of the N types of photography target parts, and differentiates a form of the shapes for a photography-completed photography target part and an unphotographed photography target part.

7. The photography support device according to claim 1, wherein the support information output unit displays, in the image-selection GUI, a candidate image group of a same photography target part, in descending order of certainty.

8. The photography support device according to claim 1, wherein, in a case in which a plurality of candidate images for a same photography target part exist, the support information output unit recommends to the photographer, in the image-selection GUI, a candidate image of which the certainty is highest.

9. The photography support device according to claim 1, wherein the support information output unit outputs, to a display with which an image-capturing device used for photography of inside of the oral cavity of the patient is equipped, information for supporting photography of the N types of photography target parts by the photographer.

10. The photography support device according to claim 1, wherein the determining unit determines, based on image features extracted from each of the plurality of images, which of the N types of photography target parts the photography target part in each image corresponds to.

11. The photography support device according to claim 1, wherein the determining unit determines, based on feature objects photographed in each of the plurality of images, which of the N types of photography target parts the photography target part in each image corresponds to.

12. The photography support device according to claim 11, wherein the feature objects include a cheek retractor, a tongue, or palate ridges.

13. The photography support device according to claim 1, wherein the determining unit determines which of the N types of photography target parts each of the plurality of images corresponds to, using a trained model that is trained to output the photography target part corresponding to an input image.

14. An image-capturing device, comprising:

the photography support device according to claim 1; and a display that displays information output from the photography support device.

15. A control method of an image-capturing device, the control method comprising:

storing an image obtained by photography of inside of an oral cavity of a patient in a storage;

determining which of N types (where N is an integer greater than 1) of photography target parts defined in advance a photography target part in the image corresponds to;

outputting a certainty that indicates a probability of determination results, along with the determination results of the photography target part in each image;

sensing, based on determination results regarding each of a plurality of images of the patient stored in the storage, whether or not shooting of images of the N types of photography target parts is complete;

outputting information for supporting photography of the N types of photography target parts by a photographer, using at least one of the determination results, and sensing results;

displaying all or part of the plurality of images as a plurality of candidate images, and outputs an image-selection graphical user interface (GUI) by which the photographer is caused to select an image from the plurality of candidate images; and displaying, in the image-selection GUI, the plurality of candidate images in a manner of being grouped by the photography target part, and displaying, in the image-selection GUI, certainty information of each candidate image along with the plurality of candidate images.

16. A non-transitory computer-readable medium that stores a program for causing a computer to execute a control method of an image-capturing device, the control method comprising:

storing an image obtained by photography of inside of an oral cavity of a patient in a storage;

determining which of N types (where N is an integer greater than 1) of photography target parts defined in advance a photography target part in the image corresponds to;

outputting a certainty that indicates a probability of determination results, along with the determination results of the photography target part in each image;

sensing, based on determination results regarding each of a plurality of images of the patient stored in the storage, whether or not shooting of images of the N types of photography target parts is complete;

outputting information for supporting photography of the N types of photography target parts by a photographer, using at least one of the determination results, and sensing results;

displaying all or part of the plurality of images as a plurality of candidate images, and outputs an image-selection graphical user interface (GUI) by which the photographer is caused to select an image from the plurality of candidate images; and displaying, in the image-selection GUI, the plurality of candidate images in a manner of being grouped by the photography target part, and displaying, in the image-selection GUI, certainty information of each candidate image along with the plurality of candidate images.

* * * * *